| United States Patent [19] | [11] | 4,173,562 |
|---|---|---|
| Bachman et al. | [45] | Nov. 6, 1979 |

[54] PROCESS FOR THE PREPARATION OF α-L-ASPARTYL-L-PHENYLALANINE METHYL ESTER

[75] Inventors: Gerald L. Bachman; Billy D. Vineyard, both of St. Louis, Mo.

[73] Assignee: Monsanto Company, St. Louis, Mo.

[21] Appl. No.: 892,358

[22] Filed: Mar. 31, 1978

Related U.S. Application Data

[63] Continuation-in-part of Ser. No. 754,297, Dec. 27, 1976, abandoned.

[51] Int. Cl.$^2$ ............................................. C07C 103/52
[52] U.S. Cl. ............................................. 260/112.5 R
[58] Field of Search ................................. 260/112.5 R

[56] References Cited

U.S. PATENT DOCUMENTS

| 3,798,207 | 3/1974 | Ariyoshi | 260/112.5 R |
| 3,933,781 | 1/1976 | Bachman et al. | 260/112.5 R |
| 3,962,207 | 6/1976 | Uchiyama et al. | 260/112.5 R |

*Primary Examiner*—Delbert R. Phillips
*Attorney, Agent, or Firm*—Robert E. Wexler

[57] ABSTRACT

A process for the preparation of α-L-aspartyl-L-phenylalanine methyl ester wherein α-L-aspartyl-L-phenylalanine is contacted with a reaction medium comprising water, methanol and a hydrogen halide to form a solid hydrogen halide salt of α-L-aspartyl-L-phenylalanine methyl ester which can be separated and converted to α-L-aspartyl-L-phenylalanine methyl ester.

9 Claims, No Drawings

PROCESS FOR THE PREPARATION OF α-L-ASPARTYL-L-PHENYLALANINE METHYL ESTER

This application is a continuation-in-part of applicant's prior copending application Ser. No. 754,297, filed Dec. 27, 1976, now abandoned.

BACKGROUND OF THE INVENTION

This invention relates to a process for the preparation of α-L-aspartyl-L-phenylalanine methyl ester (α-APM). α-APM is well known for its usefulness as a sweetening agent.

Synthesis of α-APM, according to our previous invention of U.S. Pat. No. 3,933,781, proceeds in the following general sequence of reactions:

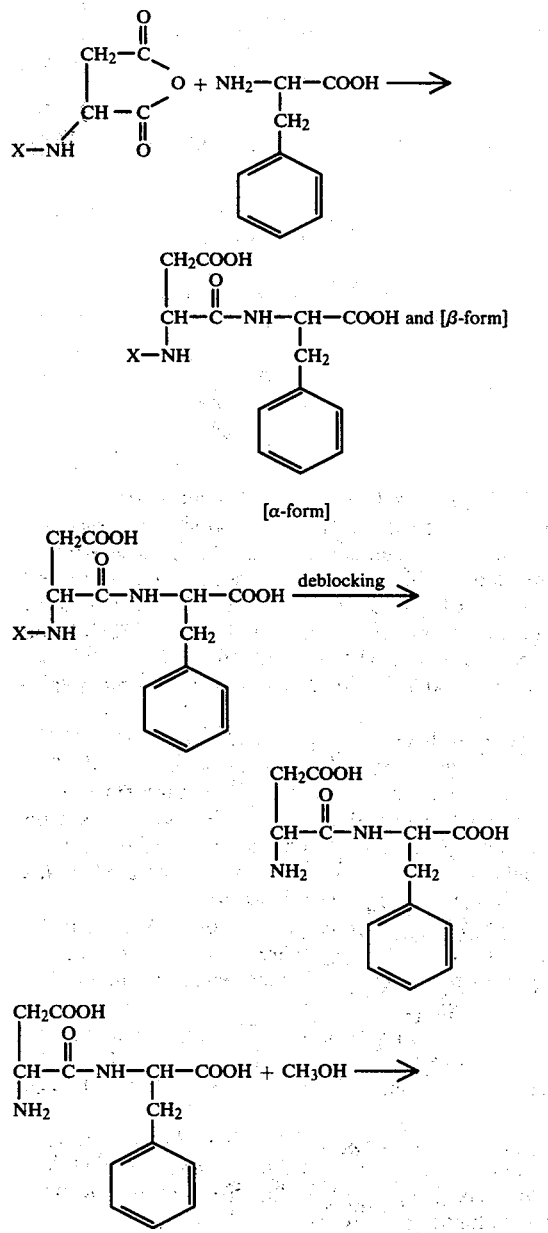
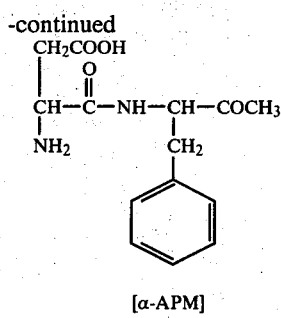

In the above equations X represents an amino protecting group.

As shown in equation (1) the starting reactants are an N-protected-L-aspartic anhydride and L-phenylalanine which are reacted to form N-protected-α-L-aspartyl-L-phenyl-alanine. The amino protecting group can be any of those known to persons skilled in the art as exemplified by formyl, acetyl, benzoyl, substituted and unsubstituted carbobenzoxy, t-butoxycarbonyl and the hydrohalide salt. Particularly preferred is N-formyl-L-aspartic anhydride.

The N-protected-α-L-aspartyl-L-phenylalanine can be separated from the N-protected-α-L-aspartyl-L-phenyl-alanine and treated to remove the protecting group to obtain α-L-aspartyl-L-phenylalanine as in equation (2). Our previous process contemplated the isolation of α-L-aspartyl-L-phenyl-alanine which was then esterified with methanol, as in equation (3), to form α-APM.

As described in U.S. Pat. No. 3,933,781, the esterification reaction was preferably "carried out with as little water present as possible". Such an esterification reaction was described for purposes of illustration as being carried out in methanol in the presence of hydrogen chloride. At that time we were of the opinion that the presence of any significant amount of water during esterification would tend to decrease the desired esterification by causing undesired deesterification reactions to occur.

A preferred method of recovering the α-APM, prepared by our procedure of U.S. Pat. No. 3,933,781, was to convert it to the HCl salt which was recovered as a solid and converted to α-APM.

Such a solid HCl salt of α-APM is also described in U.S. Pat. No. 3,798,207 which utilized it in a purification procedure for obtaining α-APM by separation from β-APM and other undesired by-products. In both of the previous procedures, the HCl salt was formed as a means of recovering α-APM after it had been prepared.

It is the primary object of this invention to provide an improved process for the preparation of α-APM.

Further objects, aspects and advantages of this invention will be apparent from the description which follows.

According to the present invention, there is provided an improved process for preparing α-APM comprising contacting α-L-aspartyl-L-phenylalanine with a reaction medium comprising water, methanol and a hydrogen halide which is hydrogen chloride or hydrogen bromide to form a solid hydrogen halide salt of α-APM, separating the solid hydrogen halide salt and converting the separated salt of α-APM.

The α-L-aspartyl-L-phenylalanine can be obtained by treating the N-protected-α-L-aspartyl-L-phenylalanine to remove the protecting group (equation 2). Any method suitable for removing protecting groups from amines is appropriate. Examples of such methods are catalytic hydrogenation and treatment with mineral acids or bases. It is preferred to remove the protecting group, particularly the formyl group, by acid hydrolysis. This hydrolysis can be carried out in, for instance, a dilute aqueous hydrochloric acid solution. The conversion to α-L-aspartyl-L-phenylalanine is usually very high, i.e., on the order of 95% or higher based on the N-protected-α-L-aspartyl-L-phenylalanine so treated. Another medium for such treatment is an acetic acid-hydrochloric acid aqueous solution.

α-L-aspartyl-L-phenylalanine can then be recovered by precipitation and liquid/solid separation. Such precipitation can, for instance, be produced by pH adjustment when the protecting group has been removed in an acid solution.

It is also possible with the process of the present invention to use the N-protected-α-L-aspartyl-L-phenylalanine to form the α-L-aspartyl-L-phenylalanine in situ in the reaction medium or to form the α-L-aspartyl-L-phenylalanine in a reaction medium without the need for isolation. A particularly preferred N-protected-α-L-aspartyl-L-phenylalanine useful in this latter manner is N-formyl-α-L-aspartyl-L-phenylalanine.

The amount of hydrogen halide useful in the reaction medium is from about 0.1 mole to about 0.80 mole per 100 grams of reaction medium. A particularly useful amount of hydrogen halide is from about 0.3 mole to about 0.7 mole per 100 grams of reaction medium. The amount of methanol useful in the reaction medium is from about 0.1 to about 1.1 moles per 100 grams of reaction medium. A particularly useful amount of methanol is from about 0.4 to about 0.6 mole per 100 grams of reaction medium.

It will be recognized by those skilled in the art that other materials may be included in the reaction medium.

The hydrogen halide present in the reaction medium must be present in an amount of from at least about 1.0 to about 20.0 moles of hydrogen halide per mole of α-L-aspartyl-L-phenylalanine being contacted. A particularly preferred amount is from about 1.15 to about 10.0 moles per mole of α-L-aspartyl-L-phenylalanine. Hydrogen chloride is the preferred hydrogen halide.

Those persons skilled in the art will recognize that the reaction medium must also contain at least about 1.0 mole of methanol per mole of α-L-aspartyl-L-phenylalanine and higher levels can also be utilized.

It should also be understood that the concentrations and amounts of materials used in the reaction medium and α-L-aspartyl-L-phenylalanine cannot practically be undertaken if undesirably excessive mixing problems are encountered.

When the α-L-aspartyl-L-phenylalanine is to be formed in situ, it has been found to be advantageous to add a lower level of hydrogen halide followed by a heating of the reaction up to about 65° C. and cooling. This causes the hydrolysis of the N-protected-α-L-aspartyl-L-phenylalanine to α-L-aspartyl-L-phenylalanine. Subsequent to such heating, further aqueous hydrogen halide can be added to the reaction mass to provide a reaction medium as described above leading to the formation of the solid hydrogen halide salt of α-APM.

The temperatures utilized should be up to about the boiling point of the reaction mass. From about 5° to about 50° C. is preferred, particularly from about 20° to about 40° C. Although most preferred temperature is near ambient temperature, it should be noted that higher temperatures tend to increase the rate of formation of α-APM but have the disadvantages of causing decomposition reactions and increasing the solubility of the hydrogen halide salts of α-APM. On the other hand, lower temperatures tend to decrease the rate of formation of α-APM, inhibit decomposition reactions and give higher levels of solid hydrogen halide salts of α-APM. One skilled in the art will recognize the need to balance those considerations to achieve the most economical temperature for the concentrations involved.

Inherent in the reaction taking place in the process of this invention is the formation of the following by-products:

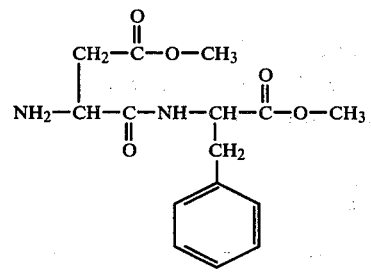

(hereinafter referred to as the "diester") and

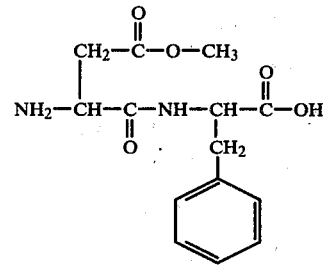

(hereinafter referred to as the "aspartyl ester").

In addition to these two by-products, the reaction mass may also contain unesterified α-L-aspartyl-L-phenylalanine. The reactions leading to the desired product and by-products are all equilibrium reactions. In the procedure of our U.S. Pat. No. 3,933,781 the isolated yields of α-APM obtained were generally from about 25 to 30% based on α-L-aspartyl-L-phenylalanine.

It has now been discovered that the process of the present invention provides a large isolated yield of α-APM. For instance, at about room temperature, as much as about 55 to 60 percent α-APM yield, based on α-L-aspartyl-L-phenylalanine, can be obtained. This is particularly surprising in view of the isolated yields obtainable in our previous procedures.

The solid hydrogen halide salt of α-APM can be recovered by solid/liquid separation procedures. Essentially all of the other compounds remain in the mother liquor and can be hydrolyzed, recovered and/or recycled to the previous reactions. The separated salt can then be converted to substantially pure α-APM for instance, as shown in U.S. Pat. Nos. 3,798,207 and 3,933,781.

The following examples are given to illustrate the instant invention in detail. It is to be understood that the specific details given in the examples are not to be construed as limiting the scope of the invention.

The materials and procedures utilized in the thin layer chromatography (TLC) analyses in the examples are as follows:

A. Plate

Silica Gel F on glass plate supplied by Brinkman Instrument In., Westbury, N.Y. 11590.

B. Solvent Systems
1. chloroform    64%  (by volume)
   methanol      30%   "
   acetic acid    2%   "
   distilled water 4%  "
2. n-propanol    70%   "
   distilled water 10% "
   methanol       1%   "
   formic acid   10%   "

C. Detection Spray Solutions
1. 0.3 g. of ninhydrin dissolved in a mixture of 100 ml. of n-butanol and 3 ml. of glacial acetic acid.
2. 1 g. of potassium iodide and 1 g. of soluble starch dissolved in 100 ml. of distilled water.

D. Procedures

After spotting and development in the appropriate solvent system the plate was air dried for 30 min.

Ninhydrin spray—The plate was sprayed and held in a 100° C. oven for 15 min.

Starch-iodide spray—The plate was placed in a chamber saturated with t-butyl hypochlorite vapor for 15 minutes, air dried for 30 min. then sprayed with freshly prepared starch-iodide solution.

EXAMPLE 1

Into a suitable vessel was charged 140 ml. of methanol and 420 ml. of 9 N hydrochloric acid which was cooled with an ice bath. The resulting solution was charged with 113.8 g. (0.4 mole) of α-L-aspartyl-L-phenylalanine (98.5% purity). Precipitation began shortly thereafter. The resulting mass was removed from the ice bath and stirred for 30 minutes causing the temperature to rise to 20° C. The resulting mass was again cooled with an ice bath, stirred for 1.5 hours resulting in substantial precipitation and then placed in a refrigerator overnight.

The next morning the reaction mass was stirred for 1 hour in an ice bath and the precipitate (130.5 grams of wet cake) was separated by filtration. The resulting cake was dissolved in 750 ml. of deionized water at 40° C. and the pH was adjusted to 4.2 over a 1.5 hour period with 36.7 g. of 50% aqueous sodium hydroxide. The resulting mass was cooled to about 5° C. and held at that temperature for 4 hours. The precipitate which was formed was separated by filtration and washed with five 30 ml. portions of 5° C. deionized water and dried. The resulting product was 51.8 grams of α-APM which is a 44% yield, based on the α-L-aspartyl-L-phenylalanine. TLC and sodium chloride analysis confirmed the purity of the α-APM product at greater than 95%.

EXAMPLE 2

To a stirred solution of 34.2 ml. (0.41 mole) of 37% hydrochloric acid, 60 ml. of water, and 40 ml. of methanol was added 110 g. (0.357 mole) of N-formyl-α-L-aspartyl-L-phenylalanine over a 20 minute period with a temperature increase from 40° to 58° C. The resulting mass was stirred at 58°-60° C. for 3 hours to allow removal of the formyl group by hydrolysis.

The reaction mass was cooled to 25° C. and 65.8 ml. (0.79 mole) of 37% hydrochloric acid was added over 10 minutes. A precipitate begins to form shortly thereafter. The resulting mass was held, while stirring, for 45 hours at ambient temperature and 1.5 hours at 5° C. causing additional precipitate to form. The solid precipitate was separated by centrifugation and the cake was washed with 100 ml. of 5° C. deionized water. The wet cake (110.2 g.) was dissolved in 410 ml. of 45° C. deionized water. The pH was adjusted to 2.5 over a 10 minute period with 80.1 g. of 4.8% aqueous sodium hydroxide and stirred for 1 hour at 40° C. While maintaining the temperature at 40°-42° C., 151.9 g. of 4.8% aqueous sodium hydroxide was added over 3 hours to raise the pH to 4.2. The mixture was stirred 1 hour at 0°-5° C. and the resulting feathery crystals were separated by centrifugation. The cake was washed with 200 ml. of 5° C. deionized water and dried overnight in a vacuum oven at 55°-60° C. The yield of α-APM was 58.3 g. (55.5% based on N-formyl-α-L-aspartyl-L-phenylalanine); $[\alpha]_D^{20} + 16.2°$ (c=4, 15 N formic acid); TLC analysis—greater than 98% pure α-APM.

EXAMPLE 3

Following essentially the same procedure as in Example 2 except that 32.5 ml. of 37% hydrochloric acid and 33.3 ml. of water was added to the reaction mass following the removal of the formyl group by hydrolysis and cooling to 25° C. gave a 33.0% yield of α-APM, based on N-formyl-α-L-aspartyl-L-phenylalanine. $[\alpha]_D^{20} + 15.3°$ (c=4, 15 N formic acid).

EXAMPLE 4

Following essentially the same procedure as in Example 2 except that the time to remove the formyl group by hydrolysis was limited to 1 hour gave a 46.2% yield of α-APM, based on N-formyl-α-L-aspartyl-L-phenylalanine. $[\alpha]_D^{20} + 15.5°$ (c=4, 15 N formic acid).

EXAMPLE 5

Following essentially the same procedure as in Example 2 except that 38.7 ml. of 37% hydrochloric acid was used in the initial solution instead of 34.2 ml. of 37% hydrochloric acid and reducing the acid introduced after hydrolysis to 61.3 ml. of 37% hydrochloric acid gave a 53.2% yield of α-APM, based on N-formyl-α-L-aspartyl-L-phenylalanine. $[\alpha]_D^{20} + 15.4°$ (c=4, 15 N formic acid).

EXAMPLE 6

Following essentially the same procedure as in Example 2 except that the holding period for causing a solid precipitate to form is increased to 4 days gave a 59.2% yield of α-APM, based on N-formyl-α-L-aspartyl-L-phenylalanine. $[\alpha]_D^{20} + 15.2$ (c=4, 15 N formic acid).

EXAMPLE 7

Following essentially the same procedure as in Example 2 except that the holding period for causing a solid precipitate to form is decreased to 1 day gave a 36.3% yield of α-APM, based on N-formyl-α-L-aspartyl-L-phenylalanine. $[\alpha]_D^{20} + 15.5$ (c=4, 15 N formic acid).

EXAMPLES 8–10

In accordance with the procedure of Example 2, α-APM was afforded using the following concentration of α-L-aspartyl-L-phenylalanine and reaction medium:

| Example | AP (Moles) | 37% HCl (Ml.) | CH$_3$OH (Ml.) | H$_2$O (Ml.) |
|---|---|---|---|---|
| 8 | 0.018 | 23.75 | 2.5 | 23.75 |
| 9 | 0.018 | 11.87 | 1.25 | 11.87 |
| 10 | 0.090 | 14.5 | 10.0 | 25.50 |

Examples 1 through 10 are tabulated in Table 1 using the previously described parameters.

Table 1

| Example No. | Methanol (moles per 100 g. reaction medium) | HCl (moles) per 100 g. reaction medium) | Moles per mol of α-L-aspartyl-L-phenylalanine* | |
|---|---|---|---|---|
| | | | Methanol | HCl |
| 1 | 0.59 | 0.65 | 8.7* | 9.45* |
| 2 | 0.48 | 0.56 | 2.8 | 3.36 |
| 3 | 0.49 | 0.38 | 2.8 | 2.24 |
| 4 | 0.48 | 0.56 | 2.8 | 3.36 |
| 5 | 0.48 | 0.56 | 2.8 | 3.36 |
| 6 | 0.48 | 0.56 | 2.8 | 3.36 |
| 7 | 0.48 | 0.56 | 2.8 | 3.36 |
| 8 | 0.11 | 0.54 | 3.3* | 16.1* |
| 9 | 0.11 | 0.52 | 1.7* | 7.80* |
| 10 | 0.49 | 0.33 | 2.8* | 1.90* |

In addition to those embodiments of the invention which are illustrated above, it is contemplated that variations thereof are within the scope of the invention. Thus, it may be possible to add other solvents or reagents to the reaction medium which will lead to equal or greater esterification efficiency and precipitation selectivity. Similarly, equivalent materials may be substituted for those specifically described. Thus, the main thrust of this invention is to esterify α-L-aspartyl-L-phenylalanine in such a manner that only the desired methyl ester will precipitate from the reaction medium, no matter what the composition of the medium. Accordingly, although the medium described herein comprises a hydrogen halide, it is contemplated that any acid or other substance which will combine with α-APM to render it insoluble in the medium, but which would not confer insolubility on other esters, would be equally effective. Similarly, if one were to prepare a derivative or complex of α-APM which is insoluble in an organic diluent, e.g. methanol, but which does not confer insolubility on other esters, the esterification could be conducted in an anhydrous medium as set forth in U.S. Pat. No. 3,933,781. Alternatively, one could conduct such anhydrous esterification and precipitate the hydrogen halide salt of α-APM by contacting the anhydrous medium with water and additional hydrogen halide.

As described above, certain intermediate products are prepared in the course of preparing α-APM. Thus, the aspartyl ester and the diester are formed and, normally, are not isolated from solution. They are allowed to take their role in the complex equilibrium reaction which affords α-APM.HCl. In the complex reaction, however, there will also be formed other intermediates and there also will be present a small amount of starting material, i.e., α-L-aspartyl-L-phenylalanine. In certain instances it may be desirable to use such intermediates as starting materials. Thus, the diester and aspartyl ester or the N-protected analogs thereof may be treated in accordance with the present invention, as may the N-protected analog of α-L-aspartyl-L-phenylalanine.

While the illustrative embodiments of the invention have been described hereinbefore with particularity it will be understood that various other modifications will be apparent to and can be readily made by those skilled in the art without departing from the spirit and scope of the invention. Accordingly, it is not intended that the scope of the claims appended hereto be limited to the Examples and descriptions set forth herein but rather that the claims be construed as encompassing all the features of patentable novelty which reside in the present invention including all features which would be treated as equivalents thereof by those skilled in the arts to which the invention pertains.

The embodiments of this invention in which an exclusive property or privilege is claimed are defined as follows:

1. A process comprising contacting α-L-aspartyl-L-phenylalanine with a reaction medium comprising from about 0.1 to about 0.8 mole hydrogen halide per 100 grams of reaction medium and from about 0.1 to about 1.1 moles methanol per 100 grams of reaction medium and water to form a solid hydrogen halide salt of α-L-aspartyl-L-phenylalanine methyl ester.

2. A process according to claim 1 wherein the α-L-aspartyl-L-phenylalanine is formed in situ from N-protected-α-L-aspartyl-L-phenylalanine by contacting N-protected-α-L-aspartyl-L-phenylalanine with the reaction medium.

3. A process according to claim 2 wherein the N-protected-α-L-aspartyl-L-phenylalanine is N-formyl-α-L-aspartyl-L-phenylalanine.

4. A process according to claim 3 wherein the reaction medium contains at least about 1.0 mole hydrogen halide and at least about 1.0 mole methanol per mole of α-L-aspartyl-L-phenylalanine.

5. A process according to claim 1 wherein the α-L-aspartyl-L-phenylalanine is prepared and contacted in unisolated form with the reaction medium.

6. A process according to claim 1 wherein the temperature during the contacting is at about the boiling point.

7. A process according to claim 1 wherein the temperature during the contacting is from about 20° to about 40° C.

8. A process according to claim 3 wherein the temperature during the removal of the formyl group does not exceed 65° C.

9. The process of claim 1 wherein the hydrogen halide is hydrogen chloride.

* * * * *

UNITED STATES PATENT AND TRADEMARK OFFICE
CERTIFICATE OF CORRECTION

PATENT NO. : 4,173,562

DATED : November 6, 1979

INVENTOR(S) : Gerald L. Bachman and Billy D. Vineyard

It is certified that error appears in the above-identified patent and that said Letters Patent are hereby corrected as shown below:

Column 5, line 14, "1%" should read -- 10% --.

Column 7, Table 1, line 14, after "phenylalanine*" insert -- or FAP --.

Signed and Sealed this

Twenty-fifth Day of March 1980

[SEAL]

Attest:

SIDNEY A. DIAMOND

Attesting Officer     Commissioner of Patents and Trademarks